United States Patent
Comini et al.

(10) Patent No.: US 9,816,116 B2
(45) Date of Patent: Nov. 14, 2017

(54) **BIOMASS OF THE MICROALGAE *SCHIZOCHYTRIUM MANGROVEI* AND METHOD FOR PREPARING SAME**

(71) Applicant: ROQUETTE FRERES, Lestrem (FR)

(72) Inventors: Serge Comini, La Gorgue (FR); Bernard Pora, Shanghai (CN)

(73) Assignee: Roquette Freres, Lestrem (FR)

( * ) Notice: Subject to any disclaimer, the term of this patent is extended or adjusted under 35 U.S.C. 154(b) by 0 days.

(21) Appl. No.: 14/766,141

(22) PCT Filed: Feb. 5, 2014

(86) PCT No.: PCT/EP2014/052214
§ 371 (c)(1),
(2) Date: Aug. 6, 2015

(87) PCT Pub. No.: WO2014/122158
PCT Pub. Date: Aug. 14, 2014

(65) Prior Publication Data
US 2016/0145656 A1    May 26, 2016

(30) Foreign Application Priority Data
Feb. 6, 2013   (FR) ..................... 13 51017

(51) Int. Cl.
| | |
|---|---|
| *C12P 7/64* | (2006.01) |
| *C12N 1/12* | (2006.01) |
| *A23L 3/3508* | (2006.01) |
| *C12R 1/89* | (2006.01) |
| *A23D 9/013* | (2006.01) |
| *C11B 1/10* | (2006.01) |
| *A23K 20/158* | (2016.01) |
| *A23L 33/115* | (2016.01) |

(52) U.S. Cl.
CPC ............ *C12P 7/6409* (2013.01); *A23D 9/013* (2013.01); *A23K 20/158* (2016.05); *A23L 33/115* (2016.08); *C11B 1/10* (2013.01); *C12N 1/12* (2013.01); *C12P 7/6427* (2013.01); *C12P 7/6463* (2013.01); *C12R 1/89* (2013.01); *A23V 2002/00* (2013.01)

(58) Field of Classification Search
None
See application file for complete search history.

(56) References Cited

U.S. PATENT DOCUMENTS

2010/0239712 A1*  9/2010  Brooks ................. A21D 2/165
                                                          426/61

FOREIGN PATENT DOCUMENTS

| EP | 0 823 475 | 2/1998 |
|---|---|---|
| WO | WO 2007/068997 | 6/2007 |
| WO | WO 2008/129358 | 10/2008 |
| WO | WO 2012/175027 | 12/2012 |
| WO | WO 2013/010090 | 1/2013 |

OTHER PUBLICATIONS

Jiang et al., "Fatty Acid Composition and Squalene Content of the Marine Microalga *Schizochytrium mangrovei*", Journal of Agricultural and Food Chemistry 2004, vol. 52, pp. 1196-1200.*
Hong et al., "Study on Biological Characteristics of Heterotrophic Marine Microalga—*Schizochytrium Mangrovei* PQ6 Isolated From Phu Quoc Island, Kien Giang Province, Vietnam", Journal of Phycology 2011, vol. 47, pp. 944-954.*
Chaung, K.-C., et al. "Effect of culture conditions on growth, lipid content, and fatty acid composition of *Aurantiochytrium mangrovei* strain BL10," *AMB Express*, Jan. 2012, vol. 2, No. 1, pp. 1-11.
Chodchoey, K., et al. "Growth, Fatty Acid Profile in Major Lipid Classes and Lipid Fluidity of *Aurantiochytrium Mangrovei* SK-02 as a Function of Growth Temperature," *Brazilian Journal of Microbiology*, Jan. 2012, vol. 43, No. 1, pp. 187-200.
Fan, K.-W., et al. "Lipid Characterization of Mangrove Thraustochytrid—*Schizochytrium mangrovei*," Journal of Agricultural and Food Chemistry, Apr. 2007, vol. 55, No. 8, pp. 2906-2910.
Written Opinion in International Application No. PCT/EP2014/052214, dated Apr. 15, 2014, pp. 1-5.

* cited by examiner

*Primary Examiner* — Michelle F Paguio Frising
(74) *Attorney, Agent, or Firm* — Blank Rome LLP

(57) ABSTRACT

The invention concerns a strain of *Schizochytrium mangrovei*, filed on 22 Nov. 2012 with the CNCM as number I-4702, having the ability to produce a high quantity of docosahexaenoic acid (or DHA) and palmitic acid, the methods for producing the corresponding biomass containing said lipid compounds of interest, and the biomass containing the products and compositions prepared from this strain.

4 Claims, No Drawings

SEQUENCE LISTING

<160> NUMBER OF SEQ ID NOS: 1

<210> SEQ ID NO 1
<211> LENGTH: 454
<212> TYPE: DNA
<213> ORGANISM: Schizochytrium mangrovei -continued

```
<400> SEQUENCE: 1
ggttttacat tgctctcatt ccgatagcaa aacgcataca cgcttcgcat cgatatttct      60
cgtcctacct cgtggagtcc acagtgggta atttacgcgc ctgctgctat ccttggatat     120
ggtagccgtc tctcaggctc cctctccgga gtcgagccct aactctccgt cacccgttat     180
agtcaccgta gtccaataca ctaccgtcga caactgatgg ggcagaaact caaacgattc     240
atcgaccaaa awagtcaatc tgctcaatta tcatgattca ccaataaaat cggcttcaat     300
ctaataagtg cagccccata cagggctctt acagcatgta ttatttccag aattactgca     360
ggtatccata taaagaaac taccgaagaa attattactg atataatgag ccgttcgcag      420
tctcacagta caatcgctta tacttacaca gcag                                 454
```

BIOMASS OF THE MICROALGAE *SCHIZOCHYTRIUM MANGROVEI* AND METHOD FOR PREPARING SAME

CROSS-REFERENCE TO RELATED APPLICATION

This application is the U.S. national stage application of International Patent Application No. PCT/EP2014/052214, filed Feb. 5, 2014.

The Sequence Listing for this application is labeled "Seq-List.txt" which was created on Jul. 17, 2015 and is 1 KB. The entire contents of the sequence listing is incorporated herein by reference in its entirety.

The present invention relates to a biomass of microalgae which is rich in docosahexaenoic acid (or DHA), palmitic acid and phospholipids, in particular phosphatidylcholine, biomass of microalgae of the *Thraustochytrium* genus, more particularly *Schizochytrium*, in the case in point the biomass of a particular strain of *Schizochytrium mangrovei*.

Lipids constitute one of the three major families of macronutrients, along with proteins and carbohydrates.

Among the lipids, triglycerides and phospholipids in particular stand out:

Triglycerides (also called triacylglycerols, triacylglycerides or TAGs) are glycerides in which the three hydroxyl groups of glycerol are esterified with fatty acids. They are the main constituent of vegetable oil and animal fats.

Triglycerides represent approximately 95% of the dietary lipids ingested by human beings. In the body, they are present mainly in adipose tissues and constitute the main form of energy storage.

Phospholipids are amphiphilic lipids, i.e., lipids consisting of a polar (hydrophilic) "head" and two aliphatic (hydrophobic) "tails".

Phospholipids are structural lipids since they are constituents of cell membranes of which they provide, inter alia, the fluidity.

Most phospholipids are phosphoglycerides, the head of which is organized around a glycerol-3-phosphate residue esterified with a polar molecule, and the two tails of which are the aliphatic chains of two fatty acids.

The other phospholipids are sphingomyelins, which derive structurally from sphingosine and not from glycerol, sphingosine constituting one of the two aliphatic tails.

The first phospholipids isolated from live tissues were characterized from egg yolk lecithin; they were more particularly phosphatidylcholines. This is, moreover, why phosphatidylcholines are also known as lecithins.

Phosphatidylcholines are naturally produced by the liver. They are an important constituent of bile, in which they emulsify the fats present in the duodenum. They are also necessary, in addition to bile salts, for preventing lipid droplets from re-agglutinating.

As phospholipids, phosphatidylcholines participate in the membranes of cells and serve to preserve their viscoelasticity. They are an essential component of the nervous system and constitute close to 30% of the dry weight of the brain and 15% of the nerves.

Triglycerides and phospholipids are composed predominantly of fatty acids which are both provided by the diet and, for some of them, synthesized by the organism.

The biochemical classification (based on the number of double bonds contained in the fatty acid molecule) distinguishes saturated fatty acids (SFAs), monounsaturated fatty acids (MUFAs) and polyunsaturated fatty acids (PUFAs).

From the physiological point of view, the following are distinguished:

indispensible fatty acids, required for development and correct functioning of the human body, but which the body is not able to produce;

"conditionally" indispensible fatty acids, which are essential for normal growth and the physiological functions of cells, but which can be produced from their precursor if it is provided by the diet, and which are therefore rigorously required if their indispensible precursor is absent; and non-indispensible fatty acids.

The set of indispensible and "conditionally" indispensible fatty acids constitutes the essential fatty acids.

The other fatty acids are termed non-essential.

Among the non-indispensible fatty acids are, in particular:

eicosapentaenoic acid (EPA) of the omega 3 fatty acid family, oleic acid, the predominant monounsaturated fatty acid in our diet, and saturated fatty acids, such as lauric acid, myristic acid or palmitic acid.

Polyunsaturated fatty acids are classified according to the position of the first double bond, starting from the final methyl function.

Thus, in the nomenclature, for omega "x" or "nx", "x" corresponds to the position of the first unsaturation.

Two major families of essential fatty acids are distinguished: omega 6 fatty acids (or n-6 PUFAs), of which the precursor and the major representative is linoleic acid (LA), and omega 3 fatty acids (or n-3 PUFAs), of which the precursor is alpha-linolenic acid (ALA).

The majority of the polyunsaturated fatty acids of biological interest belong to the omega 6 family (arachidonic acid or ARA) or omega 3 family (eicosapentaenoic acid or EPA, docosahexaenoic acid or DHA).

In addition, in the nomenclature, the carbon number constituting the chain is also defined: thus, EPA is described as C20:5 and DHA as C22:6.

The "5" and "6" thus correspond to the number of unsaturations of the carbon chain presented respectively by EPA and by DHA.

DHA, of the omega 3 fatty acid family, is a fatty acid that the organism can synthesize from alpha-linolenic acid, or which is provided by the consumption of oily fish (tuna, salmon, herring, etc.).

DHA plays an important role in the structure of membranes and in the development and function of the brain and retina.

Fish oils are used mainly as a source of omega 3 fatty acids, such as DHA and EPA, but they are also found in oils of microalgae where they are extracted either as a mixture, or separately, as is the case for example with the oils derived from certain selected strains, such as those of the *Schizochytrium* genus, which contain only traces of EPA but have high DHA contents.

Commercial preparations of biomasses of microalgae rich in DHA are available.

Mention may thus be made, for example, of:

products of the Algamac range, sold by Aquafauna Bio-Marine Inc., proposed for nutrition in rotifer aquaculture, or products sold by DSM under the brand name DHA Gold™.

However, there remains a need to provide biomasses of microalgae of quality, with a high DHA content, and having entirely specific profiles of long-chain saturated or polyunsaturated fatty acids and phospholipids.

The applicant has first of all provided a novel biomass of microalgae, rich in DHA, having:
  low contents of polyunsaturated fatty acids other than DHA (such as EPA),
  a limited content of certain long-chain saturated fatty acids (such as myristic acid and lauric acid), and
  a high content of phospholipids (up to double the amounts conventionally found in commercial preparations), more particularly of phosphatidylcholine.

a total amino acid content between 10 and 20% expressed as N×6.25 (the % being understood here to be by weight relative to 100 g of biomass at 99% of dry matter).

This strain of Schizochytrium mangrovei was deposited in France on Nov. 22, 2012 at the Collection Nationale de Cultures de Microorganismes [National Collection of Microorganism Cultures] of the Institut Pasteur (CNCM), 25 rue du docteur Roux, 75724 Paris Cedex 15, France, under number CNCM I-4702.

It was characterized by sequencing the genes encoding 18 S rRNA:

```
                                                              (SEQ ID No 1)
  1  GGTTTTACAT TGCTCTCATT CCGATAGCAA AACGCATACA CGCTTCGCAT CGATATTTCT

61  CGTCCTACCT CGTGGAGTCC ACAGTGGGTA ATTTACGCGC CTGCTGCTAT CCTTGGATAT

121  GGTAGCCGTC TCTCAGGCTC CCTCTCCGGA GTCGAGCCCT AACTCTCCGT CACCCGTTAT

181  AGTCACCGTA GTCCAATACA CTACCGTCGA CAACTGATGG GGCAGAAACT CAAACGATTC

241  ATCGACCAAA AWAGTCAATC TGCTCAATTA TCATGATTCA CCAATAAAAT CGGCTTCAAT

301  CTAATAAGTG CAGCCCCATA CAGGGCTCTT ACAGCATGTA TTATTTCCAG AATTACTGCA

361  GGTATCCATA TAAAAGAAAC TACCGAAGAA ATTATTACTG ATATAATGAG CCGTTCGCAG

421  TCTCACAGTA CAATCGCTTA TACTTACACA GCAG
```

Likewise anxious to develop a production process which is more efficient and much less expensive than those described in the prior art, the applicant has, during its research, identified a novel strain of Schizochytrium mangrovei which produces DHA and which has the particularity of producing:
  very few hypercholesterolemic saturated fatty acids (less than 6% of lauric and myristic acids, which those skilled in the art know are the most hypercholesterolemic known), and
  more than 40% of palmitic acid
(the % understood here to be by weight of total fatty acids).

Palmitic acid, also called hexadecanoic acid or cetyl acid, is one of the most common C16:0 saturated fatty acids in animals and plants.

Palmitic acid is the first fatty acid produced during lipogenesis; longer fatty acids can be produced from said palmitic acid.

Furthermore, it is the fatty acid preferentially used to synthesize ATP. The energy balance of the combustion thereof indicates 129 ATP. It thus constitutes an excellent energy food.

Industrially, palmitic acid is also used for the production of margarines and hard soaps.

In the paint field, given that it is saturated, palmitic acid cannot polymerize and becomes rigid once in contact with atmospheric oxygen (unlike oleic acid, linoleic acid and linolenic acid). It therefore remains in its soft solid form and acts (with stearic acid) as a plasticizer for polymerized oily binders. Thus, with stearic acid, it provides the elasticity required for good preservation of oil-containing pictorial materials over time.

Moreover, the biomass of Schizochytrium mangrovei according to the invention has:
  a phospholipid content between 1.5 and 2%, 1 to 1.3% of which consists of phosphatidylcholine, and which made it possible to identify it as being a strain of the Schizochytrium mangrovei type.

Consequently, the present invention relates to the strain of Schizochytrium mangrovei deposited on Nov. 22, 2012 at the CNCM under number I-4702.

This strain may subsequently be denoted "CNCM I-4702" in the present application.

The present invention also relates to a variant of this strain or to a strain derived therefrom, said variant or said derived strain conserving the property of producing high contents of DHA and palmitic acid.

In particular, it relates to a strain of Schizochytrium mangrovei obtained from the CNCM I-4702 strain by mutagenesis or by gene transformation. The mutagenesis may be site-directed and/or random. This strain conserves the property of producing high contents of DHA and palmitic acid. In particular, it is capable of producing more than 35% of DHA and more than 40% of palmitic acid, these two % being expressed by weight of total fatty acids, in particular when it is cultured under the conditions described in example 1. In addition, it produces between 1 and 1.3% of phosphatidylcholine, expressed by weight of biomass at 99% of dry matter.

The present invention also relates to a method of preparing such a strain, comprising the mutagenesis or gene transformation of the CNCM I-4702 strain and optionally a screening step for selecting the strains producing:
  more than 35% of DHA,
  more than 40% of palmitic acid (these two % expressed by weight of total fatty acids), and
  between 1 and 1.3% of phosphatidylcholine (this % expressed by weight of biomass at 99% of dry matter).

The invention relates to a method of culturing the CNCM I-4702 strain or a variant thereof conserving the capacity for producing DHA and palmitic acid, comprising a step of culturing this strain in an appropriate medium, in suitable fermentation conditions.

Moreover, the invention relates to a method for preparing the biomass of Schizochytrium mangrovei, characterized in that it is prepared by the sequence of the following steps:

culturing the strain in heterotrophic conditions so as to produce a biomass having between 35 and 40% of DHA, expressed by weight of total fatty acids, between 40 and 50 wt % of palmitic acid, expressed by weight of total fatty acids, and between 1 and 1.3% of phosphatidylcholine, % expressed by weight of biomass, collecting the biomass thus prepared, drying said biomass.

The culturing is carried out in heterotrophic conditions. Generally, the culturing step comprises a preculturing step, in order to revive the strain, then a step of culturing or fermentation proper. This latter step corresponds to the step of producing the lipid compounds of interest.

The applicant recommends, for the CNCM I-4702 strain, carrying out a three-step aerobic fermentation, as will be exemplified hereinafter.

After a prior preculturing step, the three fermentation steps are characterized by culturing the CNCM I-4702 strain in a medium in which the provision of carbon sources is regulated according to the glucose consumption by the microorganism.

It is thus noted that the glucose consumption is consumed gradually in the first hours of fermentation, and then it remains constant until the end of fermentation, as will be exemplified hereinafter.

The present invention subsequently relates to the recovery, at the end of fermentation, of the biomass rich in lipid compounds of interest, in this case DHA and palmitic acid.

After the fermentation step, the biomass is:

pasteurized, so as to inactivate the lipid-degrading enzymes (lipases) present in the biomass as such, and also in the culture medium, and recovered from the fermentation medium by any method known per se to those skilled in the art; for example, the biomass can be extracted from the fermenter and simply concentrated by microfiltration or centrifugation, or washed by a succession of concentrations/dilutions with an aqueous solution.

After fermentation, the biomass may contain:

between 35 and 40% of DHA, expressed by weight of total fatty acids, between 40 and 50 wt % of palmitic acid, expressed by weight of total fatty acids, and between 1.5 and 2% of phospholipids, 1 to 1.3% of which consists of phosphatidylcholine, % expressed by weight of biomass.

Finally, the present invention relates to the use of the biomass rich in DHA, palmitic acid and phosphatidylcholine produced by any one of the methods of the present invention, in the preparation of compositions intended for the food sector, in particular animal nutrition, but also human nutrition.

Thus, it relates to a method of preparing compositions intended for the food sector, comprising the production of a biomass rich in DHA, palmitic acid and phosphatidylcholine by any one of the methods of the present invention, then the preparation of compositions intended for the food sector.

The present invention relates in particular to a product or a composition comprising the CNCM I-4702 strain or a variant thereof conserving the capacity of producing DHA, and a biomass obtained after culturing or fermentation thereof.

Preferably, this product or composition is a food composition or a food or nutritional supplement.

It may be in liquid or solid form.

This product or composition may be in powder, granule, gel capsule, capsule or tablet form, preferably in powder form.

The invention will be understood more clearly by means of the examples which follow, which are meant to be illustrative and nonlimiting.

EXAMPLE 1

Production of a Biomass Rich in DHA and Palmitic Acid by the *Schizochytrium mangrovei* Strain CNCM I-4702

The compositions of the culture media and the fermentation conditions are given in the following tables.

TABLE 1

Composition of the culture media

| | Successive fermentors of: | | |
|---|---|---|---|
| | 100 liters | 1 m$^3$ | 10 m$^3$ |
| | Effective volume of the fermentor | | |
| | 70 liters | 700 liters | 7000 liters |
| Glucose (kg) | 6 | 41.3 | 1120 |
| Monosodium gluconate (kg) | 4.494 | 26.67 | / |
| Liquid corn steep (kg) | / | / | 119 |
| Yeast extracts (kg) | 0.448 | 2.03 | 42 |
| NaCl (kg) | 1.4 | 2.66 | 16.8 |
| KH$_2$PO$_4$ (kg) | 0.448 | 2.80 | 33.6 |
| MgSO$_4$ (kg) | 1.6 | 7.35 | 42 |
| CaCl$_2$ (kg) | 0.02 | 0.14 | 4.2 |
| NaHCO$_3$ (kg) | 0.2 | 0.07 | 4.2 |
| Antifoam (kg) (DOW FAX DF 104) | 0.112 | 1.12 | 11.2 |
| Na$_2$SO$_4$ (kg) | 0.02 | 0.07 | 42 |
| Urea (kg) | / | / | 18.9 |
| KCl (kg) | / | / | 2.8 |
| Aqueous ammonia (28%, liter) | / | / | 33.6 |
| "Red" liquid (liter) | 0.098 | 0.98 | 14 |
| "Green" liquid (liter) | 0.140 | 1.4 | 19.60 |

The initial glucose concentration in the sterilized culture medium of the 10 m$^3$ fermenter is fixed at 15 to 16 g/l.

TABLE 2

Parameters for control of the preculture and of the 3 successive fermentations

| | Preculture | 100 liters | 1 m$^3$ | 10 m$^3$ |
|---|---|---|---|---|
| Load volume | 200 ml × 3 | 70 liters | 0.7 m$^3$ | 7 m$^3$ |
| Temperature (° C.) | 28° C. | 28° C. | 28° C. | 0-68 h: 28° C. 68-80 h: 26° C. |
| pH | No | No | No regulation | Regulation 6.2~6.6 |
| Air flow rate (m$^3$/h) | — | 4.5-5.0 | 41-42 | 0-24 h: 95-105; 24-60 h: 50-60; 60-80 h: 25-30 |
| Pressure (Mpa) | — | 0.025-0.03 | 0.025-0.03 | 0.03 |
| Shaking (rpm) | 180 rpm | 120-140 | 140 | 70-75 |
| Fermentation time (h) | 48 | 24-48 | 24-48 | ~80 |

The principle for feeding with glucose during the fermentation in 10 m³ is the following:
the concentration of the glucose feed solution is 50-60%, and
when the residual glucose concentration (RCS) decreases to 1 g/l before 48 h, a solution containing 0.65 g/l of glucose is fed in one step until the glucose is exhausted and the fermentation is complete.

The results of the various fermentations are given in the following tables.

TABLE 3

First fermentation

| Time (h) | 0 | 8 | 16 | 23 |
|---|---|---|---|---|
| pH | 5.6 | 5.6 | 7.0 | 7.6 |
| Residual glucose concentration (g/100 ml) | 5.4 | / | / | 4.7 |
| Amino nitrogen (mg/100 ml) | 269 | / | / | 123 |
| Phosphorus (ppm) | 692 | / | / | 159.1 |
| Dry weight of cells (g/l) | ~0 | / | / | 29 |

TABLE 4

Second fermentation

| Time (h) | 0 | 6 h | 10 h | 14 h | 18 h | 22 h | 24 h |
|---|---|---|---|---|---|---|---|
| pH | 5.4 | 7.1 | 7.6 | 8.0 | 8.1 | 8.05 | 7.9 |
| Residual glucose concentration (g/100 ml) | 5.8 | / | / | / | / | / | 2.2 |
| Amino nitrogen (mg/100 ml) | 166 | / | / | / | / | / | 75 |
| Phosphorus (ppm) | 725.8 | / | / | / | 141.2 | / | 86.7 |
| Dry weight of cells (g/l) | 1.6 | / | / | / | / | / | 46.7 |

TABLE 5

Third fermentation

| Time (h) | 0 | 12 | 24 | 36 | 48 | 60 | 64 | 72 | 81 |
|---|---|---|---|---|---|---|---|---|---|
| pH | 6.7 | 6.3 | 5.8 | 6 | 6.2 | 6.45 | 6.5 | 6.5 | 6.6 |
| Residual glucose concentration (g/100 ml) | 14.1 | 12.1 | 9.1 | 11.2 | 9.6 | 5.8 | 5.8 | 4.35 | 1.35 |
| Amino nitrogen (mg/100 ml) | 165 | 84 | 53 | 36 | 35 | 39 | / | 37 | 31 |
| Air flow rate (m³/h) | 95-100 m³/h | | | | 60 m³/h | | | 30 m³/h | |
| Temperature (° C.) | | | | | 28 | | | | 26 |
| Phosphorus (ppm) | 724.1 | 692.4 | 661.3 | 544.3 | 599 | 659 | / | 651.2 | 618 |
| Dry weight of cells (g/l) | 11.8 | 25.7 | 37.4 | 38.5 | 44.2 | 69.9 | / | 75.4 | 80.5 |
| DHA content (%) | / | / | / | 30.7 | 27.6 | 34 | / | 32.75 | 31.4 |

Almost 70% of the amino nitrogen is consumed during the first 24 h of fermentation; the phosphorus is also consumed during the cell growth step and is no longer consumed subsequently (in connection with the regulation of the aeration flow rate and the fermentation temperature).

The level of lipid accumulation and the level of DHA production gradually increase and reach a maximum at 72 hours.

The recovery of the cells is therefore optimal as soon as this fermentation time is reached.

It is chosen to stop the fermentation at 81 h.

EXAMPLE 2

Recovery and Conditioning of the Biomass of the CNCM I-4702 Strain for Applications in Animal and Human Nutrition The biomass recovered at the end of the fermentation described in example 1 has the following composition:

TABLE 6

| Volume recovered (m³) | Dry weight of cells (g/l) | DHA content (%) |
|---|---|---|
| 7.5 | 80.5 | 31.4 |

The biomass recovered is centrifuged a first time at 6000 g, and the cells recovered are then diluted in sterile water (1.5/1 ratio) and then centrifuged a second time.

It is then subjected to a heat treatment at 70° C. for 15 minutes.

2.55 t of wet biomass (16.7% of dry matter) are recovered.

The following are added thereto for the formulations intended for animal nutrition:
2% of maltodextrin with a DE (dextrose equivalent) of 18,
0.5% of monoglycerides and diglycerides,
1% of citric acid,
0.2% of anthracyne 2727 (as antioxidant), and
0.2% of tricalcium phosphate.

For the formulations intended for human nutrition, food-grade antioxidants of tocopherol type or extracts of rosemary are used.

This biomass is spray-dried in a single-stage spray dryer (conventional running known to those skilled in the art) in the conditions given in the following Table 7:

TABLE 7

| Parameters | Values |
| --- | --- |
| Solution temperature | 65-70° C. |
| Air input temperature | 155-160° C. |
| Air output temperature | 75° C.-80° C. |
| Pressure | ~7.5 Mpa |
| Wet biomass input (kg) | 690.7 |
| Dry matter of the biomass (%) | 16.7 |
| Theoretical weight of cells (kg) | 115.35 |
| Weight of dry cells obtained (kg) | 144.03 |
| Drying yield (%) | 125 |

The composition of the dried biomass is the following (Table 8):

TABLE 8

| Parameters | Values |
| --- | --- |
| DHA content (% relative to total fatty acids) | 35.2 |
| Proteins N6.25 in g/100 g crude | 16.7 |
| Phospholipids (%) | 1.6 |
| Residual water content (%) | 1.2 |
| Ash (%) | 6.4 |
| POV (meq/kg) | 0.4 |
| P- Anisidine (%) | 23.8 |

EXAMPLE 3

Comparative Study of the Lipid Profile of a Biomass in Accordance with the Invention Compared with Those that are Commercially Available The fatty acids were determined by gas chromatography in the form of methyl esters after transesterification with methanolic hydrochloric acid and extraction with chloroform. The results are expressed as % distribution; the analysis is carried out by the internal standardization method.

A chromatograph (Varian 3800) equipped with a split-splitless injector with a tapfocus liner and a flame ionization detector was used.

An internal standard solution containing about precisely 0.5 mg of methyl heptadecanoate per ml of methanol was prepared. The methyl heptadecanoate served as a chromatographic point of reference.

About precisely 30 mg of pre-dried sample were weighed into a 6 ml tube. 1 ml of the internal standard solution and then 2 ml of 3N methanolic hydrochloric acid were added using a pipette with two measurement lines. The tube was then stoppered and placed in a dry bath thermostated at 110° C. for 4 h.

After cooling, about 0.5 ml of water and 0.5 ml of saturated aqueous sodium chloride solution were added, and extraction was carried out with 3 times 1 ml of chloroform. The chloroform phases were recovered in a 6 ml tube with them being dried on a column containing sodium sulfate. They were concentrated under a nitrogen stream to about 1 ml and injected.

The % distribution of each fatty acid (i) was obtained by the ratio of the area of the peak of this fatty acid relative to the sum of the areas of all the peaks pinpointed on the chromatogram, from lauric acid (C12:0) to DHA (C22:6 Δ4c, 7c, 10c, 13c, 16c, 19c) inclusive, with the methyl heptadecanoate peak being excluded.

The phospholipids are analyzed after disruption and cold extraction of the biomass, carried out under the following conditions.

Disruption of the Biomass

Precisely 200 mg of fresh biomass are weighed into a screw-top Pyrex tube. About 1-1.5 cm of glass beads (Retsch, reference 22.222.0003) and 0.1 ml of methanol are added. The tube is hermetically closed and stirred by means of a vortex mixer for at least 5 min.

Cold Extraction

Precisely 2 mg of triphenyl phosphate (purity ≥98%) are weighed into a small aluminum boat using a microgram balance.

The boat is placed in a Pyrex NMR tube 5 mm in diameter along with 0.9 ml of methanol and 2 ml of chloroform. The tube is hermetically closed and stirred by means of a vortex mixer for 1 min.

The tube is placed in the refrigerator. After settling out (minimum of 1 hour), the clear upper phase is carefully recovered and is transferred into a glass jar for evaporation to dryness, at ambient temperature, under a nitrogen stream.

The solid extract is dissolved in 0.5 ml of $CDCl_3$ and 0.1 ml $CD_3OD$ and transferred into an NMR tuba.

In order to express the phospholipid content on the basis of the phosphorus content obtained by NMR, the phosphorus provided by the four main phospholipids is taken into account and oleic acid is used to calculate the molar mass of each of them.

The phospholipid content is equal to the sum of the amounts of these four phospholipids thus calculated. The biomasses analyzed according to these methods (in the following Tables 9 and 10), in addition to that of the invention, are biomasses sold by Aquafauna Bio-Marine Inc., DSM/Martek and New Horizon.

TABLE 9

| | Biomass in accordance with example 2 | | ALGAMAC 3050 | | DHA Gold | | OMEGA VIE NEW HORIZON | |
|---|---|---|---|---|---|---|---|---|
| | Total fatty acids in g/100 g crude and as % relative to total fatty acids | | | | | | | |
| | g/100 g | % | g/100 g | % | g/100 g | % | g/100 g | % |
| Lauric C12:0 | 0.1 | 0.2 | 0.2 | 0.3 | 0.2 | 0.3 | <0.1 | 0.1 |
| Myristic C14:0 | 2.9 | 5.4 | 5.4 | 10.1 | 6.1 | 10.8 | 1 | 2.7 |
| Pentadecylic C15:0 | 0.3 | 0.5 | 0.2 | 0.4 | 0.2 | 0.4 | <0.1 | 0.2 |
| Palmitic C16:0 | 24.3 | 44.5 | 12.0 | 22.3 | 12.9 | 23.1 | 17.4 | 47.6 |
| Palmitoleic C16:1 Δ9c | 0.1 | 0.3 | 0.1 | 0.2 | 0.1 | 0.2 | <0.1 | 0.2 |
| Stearic C18:0 | 0.8 | 1.4 | 0.3 | 0.5 | 0.3 | 0.5 | 0.6 | 1.6 |
| Oleic C18:1 Δ9c w9 | <0.03 | | <0.03 | | <0.03 | | 0.2 | 0.5 |
| Linoleic (LA) C18:2 Δ9c, 12c w6 | <0.1 | <0.1 | <0.03 | | <0.03 | | 0.2 | 0.5 |
| g-linolenic (GLA) C18:3 Δ6c, 9c, 12c w6 | <0.1 | <0.1 | 0.1 | 0.2 | 0.1 | 0.2 | <0.03 | — |
| a-linolenic (ALA) C18:3 Δ9c, 12c, 15c w3 | <0.1 | 0.1 | <0.1 | <0.1 | <0.1 | <0.1 | 0.1 | 0.3 |
| Arachidic C20:0 | <0.1 | 0.1 | <0.1 | 0.1 | <0.1 | 0.1 | <0.1 | 0.1 |
| Stearidonic (SDA, STD) C18:4 Δ6c, 9c, 12c, 15c w3 | 0.1 | 0.2 | 0.2 | 0.3 | 0.2 | 0.3 | <0.1 | 0.2 |
| Gondoic C20:1 Δ11c w9 | <0.03 | | <0.03 | | <0.03 | | <0.03 | — |
| Dihomo-gamma-linolenic acid (DGLA) C20:3 Δ8c, 11c, 14c w6 | <0.1 | 0.1 | 0.2 | 0.3 | 0.2 | 0.3 | <0.1 | 0.1 |
| Arachidonic (AA) C20:4 Δ5c, 8c, 11c, 14c w6 | <0.1 | 0.1 | 0.2 | 0.4 | 0.2 | 0.4 | <0.1 | 0.1 |
| (ETE) C20:3 Δ11c, 14c, 17c w3 | <0.03 | | <0.03 | | <0.03 | | <0.03 | — |
| Behenic C22:0 | <0.1 | 0.1 | 0.1 | 0.2 | 0.1 | 0.2 | <0.1 | 0.1 |
| Timnodonic EPA C20:5 Δ5c, 8c, 11c, 14c, 17c w3 | 0.2 | 0.3 | 0.6 | 1.0 | 0.6 | 1.0 | 0.2 | 0.6 |
| Lignoceric C24:0 | <0.03 | | 0.1 | 0.2 | 0.1 | 0.2 | <0.03 | — |
| Osbond acid C22:5 Δ4c, 7c, 10c, 13c, 16c w6 | 4.3 | 7.9 | 8.1 | 15 | 8.0 | 14.3 | 2.7 | 7.4 |
| Nervonic C24:1 Δ15c w9 | <0.1 | <0.1 | 0.1 | 0.2 | 0.1 | 0.2 | <0.03 | — |
| Clupanodonic DPA C22:5 Δ7c, 10c, 13c, 16c, 19c w3 | <0.1 | 0.1 | 0.2 | 0.3 | 0.2 | 0.3 | <0.1 | 0.1 |
| Cervonic DHA C22:6 Δ4c, 7c, 10c, 13c, 16c, 19c w3 | 19.2 | 35.2 | 23.6 | 43.9 | 24.3 | 43.3 | 12.8 | 35 |
| Others | | <3.4 | | <4.1 | | <3.9 | | 2.6 |
| Total fatty acids | 53 | | 52 | | 54 | | | |

TABLE 10

| | Biomass in accordance with the invention according to example 1 | ALGAMAC 3050 | DHA GOLD | OMEGA VIE NEW HORIZON |
|---|---|---|---|---|
| Phospholipids in g/100 g crude, base C18:1 | 1.6 | 0.8 | 0.9 | 0.6 |
| Phosphatidylcholine as %/crude | 1.1 | 0.6 | 0.7 | 0.5 |
| Lysophosphatidylcholine as %/crude | 0.2 | 0.1 | 0.1 | 0.1 |
| Phosphatidylethanolamine as %/crude | 0.3 | 0.1 | 0.1 | <0.1 |
| Phosphatidylglycerol as %/crude | <0.1 | <0.1 | 0 | <0.1 |
| Dry matter in g/100 g | 99.1 | 98.0 | 98.5 | 97.2 |
| Ash in g/100 g crude | 6.4 | 9.5 | 10.0 | |
| Nitrogen N6.25 in g/100 g crude | 16.7 | 12.4 | 13.2 | 3.6 |

It appears, on reading the results presented here, that relative to the fatty acids profile:

the biomass according to the invention has a DHA content slightly lower than that of the commercial DHA-rich biomasses, but a palmitic acid content which is double, which constitutes as it were the fingerprint of the biomass of *Schizochytrium mangrovei* of the invention; compared with commercial oils that have an equivalent DHA content and palmitic acid content, the biomass according to the invention has double the content of phospholipids (more particularly of phosphatidylcholine); and a much higher amino nitrogen content.

The invention claimed is:

1. A method for producing a biomass of microalga containing lipid compounds of interest, the method comprising the steps of culturing a strain of *Schizochytrium mangrovei* deposited on Nov. 22, 2012 at the CNCM under number I-4702 and recovering the biomass rich in lipid compounds of interest, wherein the recovered biomass has between 35 and 40 wt % of DHA, expressed by weight of total fatty acids and between 40 and 50 wt % of palmitic acid, expressed by weight of total fatty acids.

2. The method as claimed in claim 1, characterized in that the biomass is prepared by the sequence of the following steps:
culturing the strain in heterotrophic conditions so as to produce a biomass having between 35 and 40 wt % of DHA, expressed by weight of total fatty acids and between 40 and 50 wt % of palmitic acid, expressed by weight of total fatty acids,
collecting the biomass thus prepared, and
drying said biomass.

3. A method for preparing compositions intended for the food sector comprising adding a biomass produced by the method of claim 1 to the compositions.

4. The method as claimed in claim 3, wherein said biomass comprises:
between 35 and 40 wt % of DHA, expressed by weight of total fatty acids;
between 40 and 50 wt % of palmitic acid, expressed by weight of total fatty acids; and
between 1.5 and 2 wt % of phospholipids, expressed by weight of biomass at 99% of dry matter.

* * * * *